(12) United States Patent
Higley et al.

(10) Patent No.: US 11,609,227 B2
(45) Date of Patent: Mar. 21, 2023

(54) APPARATUS AND METHOD FOR REMOTE CAPTURE OF A GENETIC SNAPSHOT OF AN AQUEOUS BODY

(71) Applicant: EQO, Inc., Austin, TX (US)

(72) Inventors: John Sanderson Wade Higley, Austin, TX (US); Erika Nicole Schwarz Taylor, Driftwood, TX (US); Stefan Karl Schuster, Austin, TX (US); Paul David Higley, Plano, TX (US)

(73) Assignee: EQO, Inc., Austin, TX (US)

( * ) Notice: Subject to any disclaimer, the term of this patent is extended or adjusted under 35 U.S.C. 154(b) by 516 days.

(21) Appl. No.: 16/736,671

(22) Filed: Jan. 7, 2020

(65) Prior Publication Data

US 2020/0217840 A1 Jul. 9, 2020

Related U.S. Application Data

(60) Provisional application No. 62/789,195, filed on Jan. 7, 2019.

(51) Int. Cl.
| | | |
|---|---|---|
| *G01N 1/14* | (2006.01) | |
| *G01N 33/53* | (2006.01) | |
| *G01N 1/16* | (2006.01) | |
| *G01N 35/10* | (2006.01) | |
| *G01N 35/00* | (2006.01) | |

(52) U.S. Cl.
CPC ........... *G01N 33/5308* (2013.01); *G01N 1/16* (2013.01); *G01N 35/1016* (2013.01); *G01N 35/1097* (2013.01); *G01N 2035/00475* (2013.01)

(58) Field of Classification Search
CPC .. G01N 33/5308; G01N 1/16; G01N 35/1016; G01N 35/1097; G01N 2035/00475; G01N 1/14; G01N 2001/1418; G01N 2001/1427; G01N 2001/1445; G01N 2001/1454
USPC ..... 73/863, 864.34, 863.71, 864.73; 700/266
See application file for complete search history.

(56) References Cited

U.S. PATENT DOCUMENTS

| | | | | | |
|---|---|---|---|---|---|
| 4,823,622 | A | * | 4/1989 | Nohl | G01N 1/28 73/864.22 |
| 5,251,495 | A | * | 10/1993 | Kuhner | G01N 1/2035 73/863.71 |
| 5,370,005 | A | * | 12/1994 | Fjerdingstad | G01N 1/2035 73/863.71 |
| 5,487,313 | A | * | 1/1996 | Johnson | G01N 35/1097 73/864.83 |
| 5,600,075 | A | * | 2/1997 | Peterson | G01N 1/22 73/863.71 |
| 8,196,479 | B2 | * | 6/2012 | Ludwick | G01N 1/2273 73/863.25 |

* cited by examiner

*Primary Examiner* — Robert R Raevis

(57) ABSTRACT

A field apparatus (also referred to as a "biosampler") is configured to automatically capture multiple samples of an aqueous medium (for example, water from a lake) and process same to preserve unstable analytes in the field. In this way, a set of samples from the aqueous medium can, for example, be captured at multiple points in time, processed with a biopreservative to preserve unstable analytes (for example, RNA) and then later collected for further analysis. Alternatively, multiple samples of the aqueous medium can be collected and preserved at one moment.

20 Claims, 6 Drawing Sheets

```
┌─────────────────────────────────────────────┐
│ CONTROL ELECTRONICALLY CONTROLLED SWITCHING │
│ VALVE, INLET VALVE AND OUTLET VALVE TO ALLOW A │ — 610
│ VOLUME OF A FIRST LIQUID TO PASS THROUGH SAMPLE │
│ COLLECTION VESSEL │
└─────────────────────────────────────────────┘
                      │
                      ▼
┌─────────────────────────────────────────────┐
│ CONTROL ELECTRONICALLY CONTROLLED SWITCHING │
│ VALVE, INLET VALVE AND OUTLET VALVE TO ALLOW A │ — 620
│ VOLUME OF A SECOND LIQUID TO PASS THROUGH │
│ SAMPLE COLLECTION VESSEL │
└─────────────────────────────────────────────┘
                      │
                      ▼
┌─────────────────────────────────────────────┐
│ CLOSE ELECTRONICALLY CONTROLLED INLET VALVE │ — 630
│ AND ELECTRONICALLY CONTROLLED OUTLET VALVE │
└─────────────────────────────────────────────┘
```

APPARATUS AND METHOD FOR REMOTE CAPTURE OF A GENETIC SNAPSHOT OF AN AQUEOUS BODY

CROSS REFERENCE TO RELATED APPLICATION AND CLAIM OF PRIORITY

This application claims priority under 35 U.S.C. § 119(e) to U.S. Provisional Patent Application No. 62/789,195 filed on Jan. 7, 2019. The above-identified provisional patent application is hereby incorporated by reference in its entirety.

TECHNICAL FIELD

This disclosure relates generally to environmental testing of aqueous bodies, such as lakes, rivers, pools and oceans. More specifically, this disclosure relates to an apparatus and method for remote capture of a genetic snapshot of an aqueous body.

BACKGROUND

We are water and carbon based-lifeforms and residents of a planet, 70% of whose surface area is covered in water. Accordingly, the health of our planet's water is an issue of unexaggerable concern to all life on earth. In the face of factors such as population growth, climate change, and unforeseen migrations of species (for example, in the holds of international air flights, or bilges of container ships) to unfamiliar ecosystems, effective stewardship of our planet's water resources requires data that is comprehensive, up-to-date, detailed and from which trends can be determined. Put differently, the health of any given body of water can no longer be assumed from past measurements or surveys of the species present in the water. As shown by, for example, the explosive growth of zebra mussel populations from a first sighting in 2009 to invasive levels in certain Texas lakes in 2017, changes in the health and balance of species in bodies of water can be extremely rapid and unforeseeable.

The challenges of gathering large sets of current, nuanced data needed for effective data-driven stewardship of our planet's water resources include, without limitation, the fact that water is a relatively dense medium. Thus, while aqueous samples of tens of gallons can provide high resolution data as to a body of water, for field measurements, the tendency is to collect small (e.g., test tube or sample bottle sized) samples, given the density of water.

Further, the challenges associated with increasing the number of bodies of water sampled and the quantities, in gallons, of water sampled at each body of water include a shortage of human resources (for example, a limited number of scientists and technicians to collect samples), geographic challenges (for example, certain bodies of water are far away from electricity and laboratories), and the instability of certain analytes of interest. Ribonucleic acid (RNA) presents one example of an unstable analyte of interest. RNA in the particulate matter of an aqueous sample can, for example, provide a snapshot of the current status within the life and breeding cycles of the life within a body of water from which useful insights as to population trends and the effectiveness of stewardship efforts (for example, rinsing mussels from the hulls of watercraft) can be derived. However, RNA breaks down quickly, meaning that, for an RNA analysis to be performed, a sample must be promptly treated with a biopreservative to arrest the breakdown of RNA in the sample.

Traditional methods of obtaining samples of aqueous media, such as humans filling sample bottles and returning the samples to laboratories for further analysis, are inadequate for generating data on the scale and level of detail to address the challenges of protecting our planet's many and geographically dispersed bodies of water.

SUMMARY

This disclosure provides an apparatus and method for remote capture of a genetic snapshot of an aqueous body.

In a first embodiment, a field apparatus for remotely capturing an unstable analyte in a sample of an aqueous medium includes a sample collection vessel, which has an inlet portion, an outlet portion, and a plenum comprising a filter, the filter disposed between the inlet and outlet portions. The field apparatus further includes an electronically controlled inlet valve configured to control passage of liquid into the sample collection vessel via the inlet portion, and an electronically controlled outlet valve configured to control the passage of liquid out of the sample collection vessel via the outlet portion. Additionally, the field apparatus has an electronically controlled switching valve configured to provide one of a first liquid or a second liquid to the electronically controlled inlet valve, and an acquisition controller. The acquisition controller is configured to control the electronically controlled switching valve, electronically controlled inlet valve, and electronically controlled outlet valve to allow a volume of the first liquid to pass through the sample collection vessel, control the electronically controlled switching valve, electronically controlled inlet valve, and electronically controlled outlet valve to allow a volume of the second liquid to pass through the sample collection vessel, and close the electronically controlled inlet valve and electronically controlled outlet valve.

In a second embodiment, a method of remotely capturing an unstable analyte in a sample of an aqueous medium includes controlling an electronically controlled switching valve, an electronically controlled inlet valve, and an electronically controlled outlet valve of a field apparatus to allow a volume of a first liquid to pass through a sample collection vessel, the sample collection vessel comprising an inlet portion, an outlet portion and a plenum comprising a filter, the filter disposed between the inlet and outlet portions. The method further includes controlling the electronically controlled switching valve, electronically controlled inlet valve, and electronically controlled outlet valve to allow a volume of a second liquid to pass through the sample collection vessel, and closing the electronically controlled inlet valve and electronically controlled outlet valve. According to the second embodiment, the electronically controlled inlet valve is configured to control passage of liquid into the sample collection vessel via the inlet portion. Further, the electronically controlled outlet valve is configured to control the passage of liquid out of the sample collection vessel via the outlet portion. Additionally, the electronically controlled switching valve is configured to provide one of a first liquid or a second liquid to the electronically controlled inlet valve.

In a third embodiment, a non-transitory computer-readable medium includes program code, which when executed by a processor, causes a field apparatus to control an electronically controlled switching valve, an electronically controlled inlet valve, and an electronically controlled outlet valve of a field apparatus to allow a volume of a first liquid to pass through a sample collection vessel, the sample collection vessel having an inlet portion, an outlet portion and a plenum having a filter, the filter disposed between the inlet and outlet portions. Additionally, the program code, when executed by the processor, causes the field apparatus to control the electronically controlled switching valve, electronically controlled inlet valve, and electronically controlled outlet valve to allow a volume of a second liquid to pass through the sample collection vessel; and close the electronically controlled inlet valve and electronically controlled outlet valve. In the third embodiment, the electronically controlled inlet valve is configured to control passage of liquid into the sample collection vessel via the inlet portion, the electronically controlled outlet valve is configured to control the passage of liquid out of the sample collection vessel via the outlet portion, and the electronically controlled switching valve is configured to provide one of a first liquid or a second liquid to the electronically controlled inlet valve.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "controller" means any device, system or part thereof that controls at least one operation. Such a controller may be implemented in hardware or a combination of hardware and software and/or firmware. The functionality associated with any particular controller may be centralized or distributed, whether locally or remotely. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Definitions for other certain words and phrases are provided throughout this patent document. Those of ordinary skill in the art should understand that in many if not most instances, such definitions apply to prior as well as future uses of such defined words and phrases.

BRIEF DESCRIPTION OF THE DRAWINGS

For a more complete understanding of this disclosure and its advantages, reference is now made to the following description, taken in conjunction with the accompanying drawings, in which.

DETAILED DESCRIPTION

FIGS. 1 through 6, discussed below, and the various embodiments used to describe the principles of this disclosure in this patent document are by way of illustration only and should not be construed in any way to limit the scope of the disclosure. Those skilled in the art will understand that the principles of this disclosure may be implemented in any suitably arranged wireless communication system.

Figure 1:
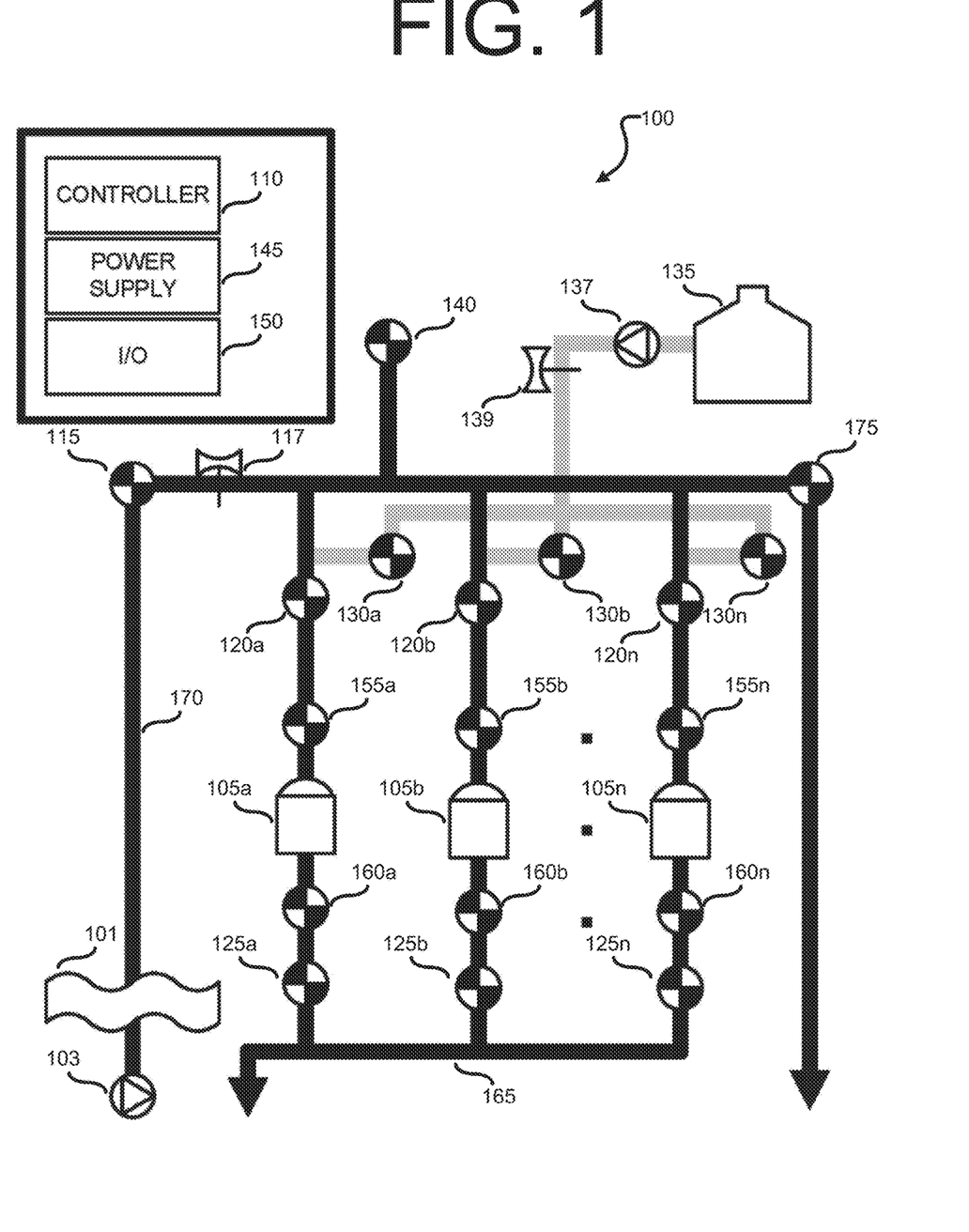
FIG. 1 illustrates, in schematic view, an example of a field apparatus configured for use according to certain embodiments of this disclosure.

FIG. 1 illustrates, in schematic view, an example of a field apparatus 100 configured for use according to certain embodiments of this disclosure.

According to various embodiments, field apparatus 100 (also referred to as a "biosampler") is configured to automatically capture multiple samples of an aqueous medium 101 (for example, water from a lake) and process same to preserve unstable analytes in the field. In this way, a set of samples from the aqueous medium can, for example, be captured at multiple points in time, processed with a biopreservative to preserve unstable analytes (for example, RNA) and then later collected for further analysis. Alternatively, multiple samples of the aqueous medium can be collected and preserved at one moment. Embodiments according to this disclosure facilitate the automated collection and preservation of large samples of aqueous media (thereby making it easier to detect trace or low concentration analytes), as well as samples (also referred to herein as "snapshots") at multiple points in time. As such, some embodiments according to this disclosure facilitate the production of sample sets which have a high resolution (based on a large volume of aqueous media) or provide information across multiple points of time. Improvements (for example, in terms of quantity and range of times) in sample collection provided by certain embodiments according to this disclosure, translate into bigger and better data regarding conditions in the aqueous medium, which in turn, translates into improvements in the analytical tools which can be applied to the study of the health of bodies of water. For example, embodiments according to this disclosure can be used to generate data sets of sufficient size with information on a wide range of variables, to effectively apply "big data" analyses to issues of water health.

Referring to the non-limiting example of FIG. 1, field apparatus 100 comprises a plurality of sample collection vessels numbered 105a through 105n, an acquisition controller 110, a plurality of electronically controlled inlet valves 120a through 120n, a plurality of electronically controlled outlet valves 125a through 120n, and a plurality of electronically controlled switching valves 130a through 130n. According to certain embodiments, field apparatus 100 comprises, or is connected to, inlet valve 115, inlet flow meter 117, biopreservative reservoir 135, biopreservative pump 137, and flow meter 139. In some embodiments, field apparatus 100 comprises, or is connected to, sample pump 103, air valve 140, power supply 145 and input/output interface 150. Additionally, in certain embodiments, field apparatus 100 further comprises manually controlled inlet valves 155a through 155n, manually controlled outlet valves 160a through 160n, drain line 165, inlet line 170 and flush valve 175.

According to certain embodiments, acquisition controller 110 is a microcontroller or other apparatus comprising a non-transitory memory (for example, a solid state drive or programmable read-only-memory), a processor, and an output interface (for example, output pins) capable of providing control signals to one or more electronically controlled valves either directly or indirectly (for example, via a relay or input/output interface). According to various embodiments, the output interface of acquisition controller 110 further supports a display (for example, a liquid crystal display with a 16-pin interface) providing status and selection information to a user. According to certain embodiments, acquisition controller 110 further includes an input interface (for example, pins on a microcontroller) for receiving inputs, examples of which include, without limitation, user inputs provided by a keypad or buttons of acquisition controller 110, sensor data (for example, temperature data from a digital thermometer, or flow data from inlet flow meter 117 or flow meter 139, or a battery meter associated with power supply 145), or data received over a wired or wireless network via input/output interface 150. Microcontrollers suitable for use in acquisition controller 110 include, without limitation, microcontrollers of the ARM® CORTEX® series of microcontrollers or the ATMEL ATmega328 microcontroller. As shown in the non-limiting example of FIG. 1, acquisition controller 110 implements control logic to control the operation of electronically controlled valves (for example, electronically controlled inlet valves 120a through 120n) to capture and preserve samples of aqueous medium 101 in sample collection vessels 105a through 105n. As discussed in this disclosure, in certain embodiments, acquisition controller 110 also implements conditional control logic for enhancing the performance and reliability of field apparatus, by for example, implementing a "freeze mode" for when the air temperature is measured as being below freezing.

In various embodiments according to this disclosure, the plurality of sample collection vessels 105a through 105n comprise open-ended vessels made of polyvinylchloride, polypropylene, glass, or other nonporous materials, which comprise a plenum disposed between an inlet portion and an outlet portion. According to certain embodiments, each sample collection vessel of the plurality of sample collection vessels 105a through 105n is constructed (for example, by constructing the plenum as a pair of threaded halves) to facilitate the insertion and removal of one or more filters spanning an interior circumference of the plurality of collection vessels. As shown in the non-limiting example of FIG. 1, the plurality of sample collection vessels are designated 105a, 105b and 105n, with a vertical ellipsis between sample collection vessel 105b and 105n. As used in this disclosure, the combination of discontinuous letter designation and vertical ellipsis are to emphasize that, for field apparatus according to this disclosure, the number of sample collection vessels can vary across embodiments.

As shown in the non-limiting example of FIG. 1, field apparatus 100 comprises a plurality of electronically controlled inlet valves 120a through 120n. In the non-limiting example of FIG. 1, electronically controlled inlet valve 120a operates to allow or block the passage of liquid (for example, a biopreservative or a sample of aqueous medium 101) into sample collection vessel 105a.

According to various embodiments, each electronically controlled inlet valve (for example, electronically controlled inlet valve 120a) is an electronically actuated ball valve which opens and closes in response to a control signal provided by, or initiated by (for example, in embodiments utilizing relays or an input/output interface) acquisition controller 110. In certain embodiments, electronically controlled inlet valve 120a is a motorized ball valve. In some embodiments electronically controlled inlet valve 120b is actuated via a solenoid. According to certain embodiments, each of electronically controlled inlet valves 120a through 120n is coupled directly or indirectly (for example, with a manually controlled valve in between) to an inlet portion of a sample collection vessel (for example, sample collection vessel 105a). According to some embodiments, electronically inlet valve 120a includes a handle or other mechanism for mechanical actuation of the valve.

According to certain embodiments, field apparatus 100 comprises a plurality of electronically outlet valves 125a through 125n. In the non-limiting example of FIG. 1, electronically controlled outlet valve 125a operates to allow or block the passage of liquid (for example, a biopreservative or a sample of aqueous medium 101) out of sample collection vessel 105a.

As emphasized by the vertical ellipsis and numbering scheme used in FIG. 1, the number of outlet valves, like the number of sample collection vessels and electronically controlled inlet valves, varies across embodiments and intended applications. In some embodiments, each sample vessel has its own electronically controlled inlet valve and its own electronically controlled outlet valve. In certain embodiments, inlet or outlet switching for multiple sample collection vessels can be handled by a single valve (for example, a multi-way valve). According to various embodiments, each electronically controlled outlet valve (for example, electronically controlled outlet valve 125a) is an electronically actuated ball valve which opens and closes in response to a control signal provided by, or initiated by (for example, in embodiments utilizing relays) acquisition controller 110. In certain embodiments, electronically controlled outlet valve 125a is a motorized ball valve. In some embodiments electronically controlled outlet valve 125a is actuated via a solenoid. According to certain embodiments, each of electronically controlled outlet valves 125a through 125n is coupled directly or indirectly (for example, with a manually controlled valve in between) to an outlet portion of a sample collection vessel (for example, sample collection vessel 105a). According to some embodiments, electronically controlled outlet valve 125a includes a handle or other mechanism for mechanical actuation of the valve.

Referring to the non-limiting example of FIG. 1, field apparatus 100 includes a plurality of electronically controlled switching valves 130a through 130n. According to some embodiments, electronically controlled switching valve 130a is a motorized ball valve. Once again, for the purposes of describing the explanatory example of FIG. 1, the vertical ellipsis in the figure and numbering of the electronically controlled switching valves are to emphasize that, in embodiments according to this disclosure, the number of electronically controlled switching valves is variable. In certain embodiments, each sample collection vessel is associated with its own electronically controlled switching valve. In some embodiments, one or more multi-way valves may be used instead. In the non-limiting example of FIG. 1, electronically controlled switching valve 130a operates in response to control signals provided or initiated by acquisition controller to switch between sources of liquid media passing through sample collection vessel 105a. As a non-limiting example, electronically controlled switching valve 130a operates to change between sourcing a first liquid (for example, aqueous medium 101) and a second liquid (for example, a biopreservative stored in biopreservative reservoir 135) and a second liquid through sample collection vessel 105a.

As shown in the illustrative example of FIG. 1, field apparatus 100 comprises a plurality of manually controlled inlet valves 155a through 155n. According to certain embodiments, manually controlled inlet valve 155a acts as a manual backup to electronically controlled inlet valve 120a, preventing the passage of liquid through sample collection vessel 105a in the event that electronically controlled inlet valve 120a fails and remains stuck in an open position. In some embodiments, manually controlled inlet valve 155a is configured to be attached to the inlet portion of sample collection vessel 105a, and readily detachable from field apparatus 100. In such embodiments where sample collection vessel 105a is detachable, manually controlled inlet valve 155a acts as a barrier to keep contaminants away from a preserved sample in sample collection vessel 105a.

In various embodiments according to this disclosure, field apparatus 100 comprises a plurality of manually controlled outlet valves 160a through 160n. According to certain embodiments, manually controlled outlet valve 160a acts as a manual backup to electronically controlled outlet valve 125a, preventing the passage of liquid from sample collection vessel 105a in the event that electronically controlled outlet valve 125a fails and remains stuck in an open position. In some embodiments, manually controlled outlet valve 160a is configured to be attached to the outlet portion of sample collection vessel 105a, and readily detachable from field apparatus 100. In such embodiments where sample collection vessel 105a is detachable, manually controlled outlet valve 160a acts as a barrier to keep contaminants away from a preserved sample in sample collection vessel 105a.

As illustrated in the example of FIG. 1, field apparatus 100 includes a biopreservative reservoir 135, which is a sealed container holding a volume of biopreservative (for example, RNALATER®), which is provided, along paths variously comprising electronically switching valves 130a through 130n to sample collection vessels 105a through 105n. Depending on embodiments, biopreservative reservoir 135 is insulated (for example, in a housing shared with the sample collection vessels 105a through 105n) against changes in temperature and light. In certain embodiments, biopreservative reservoir 135 comprises a plurality of containers, as a safeguard against leakage or damage to a container.

According to certain embodiments, a biopreservative pump 137 is provided downstream of biopreservative reservoir 135 to deliver, or control the delivery of biopreservative to switching valves 130a through 130n. In certain embodiments, biopreservative pump 137 is powered by power supply 145 and controlled by control logic implemented at acquisition controller 110. In various embodiments, biopreservative pump comprises a peristaltic pump or low flow pump configured to provide precise control of the volume of biopreservative passing to switching valves 130a through 130n. In some embodiments, switching valves 130a through 130n are gravity fed and biopreservative pump 137 can be omitted or bypassed.

As shown in the illustrative example of FIG. 1, the fluid path from biopreservative reservoir 135 to switching valves 130a through 130n includes a flow meter 139, to provide measured data on the volume of biopreservative passing along to switching valves 130a through 130n. In this way, each sample captured by field apparatus 100 can be consistently treated with a measured quantity of biopreservative. In certain embodiments, flow meter 139 provides analog data regarding measured fluid flows to input/output interface 150, which in turn digitizes and relays the flow data to acquisition controller 110.

In various embodiments according to this disclosure, field apparatus 100 comprises a sample pump 103. In the illustrative example of FIG. 1, sample pump 103 comprises a battery powered submersible pump with can be disposed at a point of interest (for example, at a particular depth, or proximity to the surface or floor of a body of water) within aqueous medium 101. In various embodiments, sample pump 103 is powered by power supply 145, and controlled by control signals provided by, or initiated by acquisition controller 110.

In certain embodiments, samples of aqueous medium 101 are pumped by sample pump 103 via inlet line 170 to inlet valve 115. As shown in the non-limiting example of FIG. 1, inlet line 170 comprises one or more sections of rugged hose or pipe capable of supporting fluid flows on the order of approximately 3 gallons a minute (for example, in embodiments where ~100 gallons of aqueous medium are passed through a sample collection vessel over ~30 minutes).

As shown in the illustrative example of FIG. 1, inlet valve 115 controls the passage of aqueous medium 101 from inlet line 170 to electronically controlled inlet valves 120a through 120n. According to certain embodiments, inlet valve 115 is an electronically controlled valve of similar construction and operation to the valves comprising electronically controlled inlet valves 120a through 120n. For example, in some embodiments, inlet valve 115 is an electronically actuated ball valve which opens and closes in response to control signals provided, or initiated, by acquisition controller 110. In some embodiments, inlet valve 115 can be closed to prevent the entry of aqueous medium during flush or freeze protection cycles initiated by acquisition controller 110.

According to certain embodiments, an inlet flow meter 117 is disposed downstream of inlet valve 115 to provide data regarding the flow of aqueous medium into one or more of sample collection vessels of the plurality of sample collection vessels. As shown in the non-limiting example of FIG. 1, inlet flow meter 117 is a digital flow meter which provides flow data directly to acquisition controller 110. In some embodiments, inlet flow meter 117 provides flow data to acquisition controller 110 via input/output interface 150.

Referring to the non-limiting example of FIG. 1, field apparatus 100 includes air valve 140 and drain valve 175 (also referred to herein as a "flush valve"). According to certain embodiments, acquisition controller 110 implements drain and flush cycles for a variety of purposes, including, without limitation, purging the lines of field apparatus of aqueous medium and/or biopreservative between sample cycles (to prevent dilution of biopreservative or premature dosing of a sample with biopreservative), or to protect the lines of field apparatus 100 from freeze damage. In certain embodiments, both air valve 140 and drain valve 175 are electronically controlled valves of similar construction and operation to other electronically controlled valves of field apparatus 100 (for example, electronically controlled outlet valve 125a). In some embodiments, actuation of drain valve 175 causes liquid in field apparatus 100 to pass to drain line 165. Depending on, for example the chemical hazards, if any, of the biopreservative in biopreservative reservoir 135, drain line 165 may feed back into the body of water from which a sample of aqueous medium 101 was drawn, ground near field apparatus 100, or a drainage collection tank.

According to further embodiments, field apparatus 100 comprises, or is connected to a power supply 145. In some embodiments, power supply 145 comprises one or more batteries capable of holding sufficient charge to power acquisition controller 110, and the valves and pumps of field apparatus over a test cycle in the field. According to certain embodiments, the length of a test cycle may range from 30 minutes or less (for example, a test cycle in which all of the samples are collected contemporaneously) to two or more weeks (for example, when one sample is collected a day, and with sample collection being delayed by triggering freeze protection). In certain embodiments, power supply 145 further comprises a solar panel, wind turbine or other source of electrical energy which can generate electricity in the field.

In various embodiments according to this disclosure, field apparatus 100 includes an input/output interface 150, which operates as an intermediary between acquisition controller 110 and components of field apparatus 100 operating under the control of field apparatus 100 (for example, inlet valve 115) as well as components providing feedback or other data to be used by field apparatus 100 (for example, inlet flow meter 117, or a thermometer (not shown)). As shown in the non-limiting example of FIG. 1, input/output interface comprises one or more interface units utilizing the RS-485 protocol (for example, modules from the "Adam" series of RS-485 modules by Advantech Co., Ltd.). According to certain embodiments, input/output controller provides and receives, from acquisition controller 110, processor level signals (for example, low current, digital signals), and provides and receives, from the components and sensors connected to acquisition controller 110, component level signals (for example, analog signals from flow meter 139, and signals with sufficient power and current to control the operation of electronically controlled outlet valve 125a. In various embodiments according to this disclosure, input/output interface 150 also includes a wired or wireless network interface (for example, a WI-FI, BLUETOOTH®, or long term evolution "LTE") for passing data and status information to other networked devices.

Figure 2:
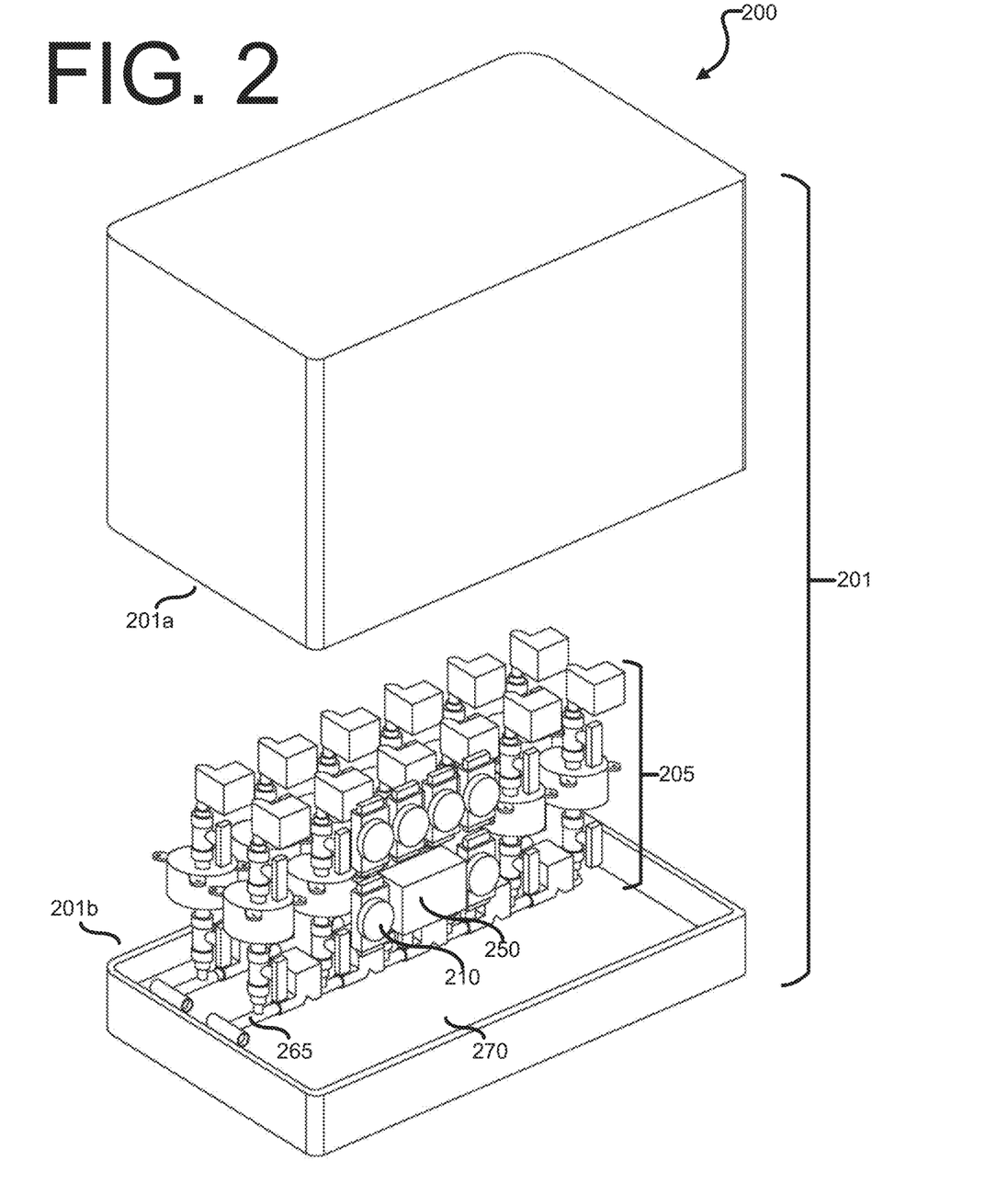
FIG. 2 illustrates an example of a field apparatus according to some embodiments of this disclosure.

FIG. 2 illustrates an example of a field apparatus 200 according to some embodiments of this disclosure. As shown in the non-limiting example of FIG. 2, in certain embodiments, field apparatus 200 comprises upper (for example, upper half 201a) and lower halves (for example, lower half 201b) of a protective enclosure 201.

Referring to the non-limiting example of FIG. 2, protective enclosure 201 is constructed of one or more materials selected as providing a suitable combination of protection for the contents of protective enclosure and desirable thermal properties. In certain embodiments, for example, embodiments intended to be used in cold climates, protective enclosure 201 may comprise a hard plastic shell with an insulating foam layer. In some embodiments, including, for example, embodiments in hotter environments or environments with large animals, protective enclosure may be made of perforated steel, to withstand animal attack and heat buildup in the enclosure.

As shown in the illustrative example of FIG. 2, protective enclosure 201 houses a plurality of sample collection vessel "stacks" 205 of field apparatus 200. In this example, protective enclosure 201 contains twelve such sample collection vessel stacks, though embodiments with as few as one, or many more, sample collection vessel stacks are within the contemplated scope of this disclosure. In certain embodiments, volumes of liquid (for example, aqueous medium 101 in FIG. 1) are provided to sample collection vessel stack 205 via one or more inlet lines (not shown) disposed above or upstream of an electronically controlled inlet valve (for example, electronically controlled inlet valve 120a in FIG. 1) of the stack, and exit sample collection vessel stack 205 via one or more drain lines 265.

According to certain embodiments, protective enclosure 201 houses an acquisition controller 210, and one or more input/output interfaces 250. As shown in the non-limiting example of FIG. 2, in addition to the aforementioned components, protective enclosure 201 includes a volume of reserved space 270. According to some embodiments, reserved space 270 is used for housing one or more reservoirs of biopreservative (for example, biopreservative reservoir 135 in FIG. 1), a battery or other power supply (for example, power supply 145 in FIG. 1), or additional pumps or valve gear (for example, switching valves 130a through 130n in FIG. 1).

Figure 3:
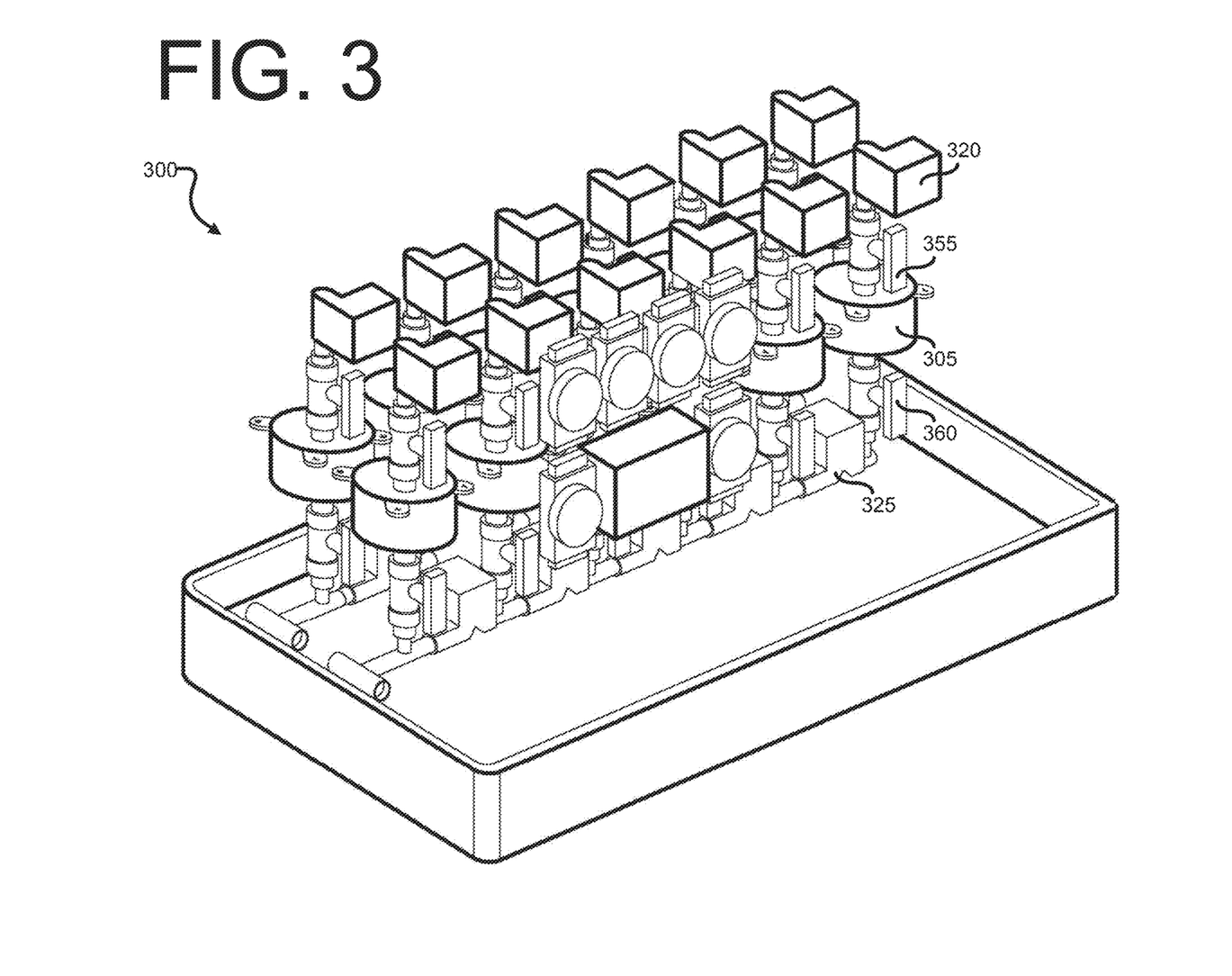
FIG. 3 illustrates an example of a field apparatus according to various embodiments of this disclosure.

FIG. 3 illustrates an example of a field apparatus 300 according to various embodiments of this disclosure. Referring to the non-limiting example of FIG. 3, field apparatus 300 is shown without a protective enclosure (for example, upper half 201a in FIG. 2). Depending on embodiments, the field apparatus may be deployed in a vehicle, temporary structure, or other context where a full enclosure (for example, protective enclosure 201

In the non-limiting example of FIG. 3, the elements of a sample collection vessel stack (for example, sample collection vessel stack 205 in FIG. 2) according to certain embodiments are illustrated. In certain embodiments, sample collection vessel 305 comprises a removable middle element of a sample collection vessel stack. In some embodiments, (for example, embodiments where analytes of interest are found in particulate matter in an aqueous sample) sample collection vessel 305 provides a sealed vessel containing one or more filters (for example, sheets of filter paper having different mesh sizes, such as 50 micron and 25 micron mesh) through which a volume of water (which can exceed the volume of sample collection vessel 305) passes through, leaving particulate matter on the filter(s) therein.

According to various embodiments, sample collection vessel 305 comprises an inlet portion, through which liquids (such as aqueous media and biopreservative) enter the sample collection vessel. In certain embodiments, the inlet portion comprises, or is connected to a manual inlet valve 355. As shown in FIG. 3, manual inlet valve is disposed between sample collection vessel 305 and electronically controlled inlet valve 320, and operates both as a manual backup to electronically controlled inlet valve 320, and, in embodiments where sample collection vessel 305 is removable, to seal off sample collection vessel 305 for storage or transit to a facility for analyzing the preserved sediment within sample collection vessel 305.

In some embodiments, a sample vessel collection stack include manual outlet valve 360, which comprises, or is connected to, an outlet portion of sample collection vessel 305. As shown in the illustrative example of FIG. 3, manual outlet valve 360 provides both a manual backup to electronically controlled outlet valve 325 and a protective seal (both to protect a captured sample and to keep a clean vessel from being contaminated) of sample collection vessel 305 when sample collection vessel 305 is removed for transit.

According to various embodiments, the sample collection vessel stack further comprises electronically controlled outlet valve 325.

Figure 4:
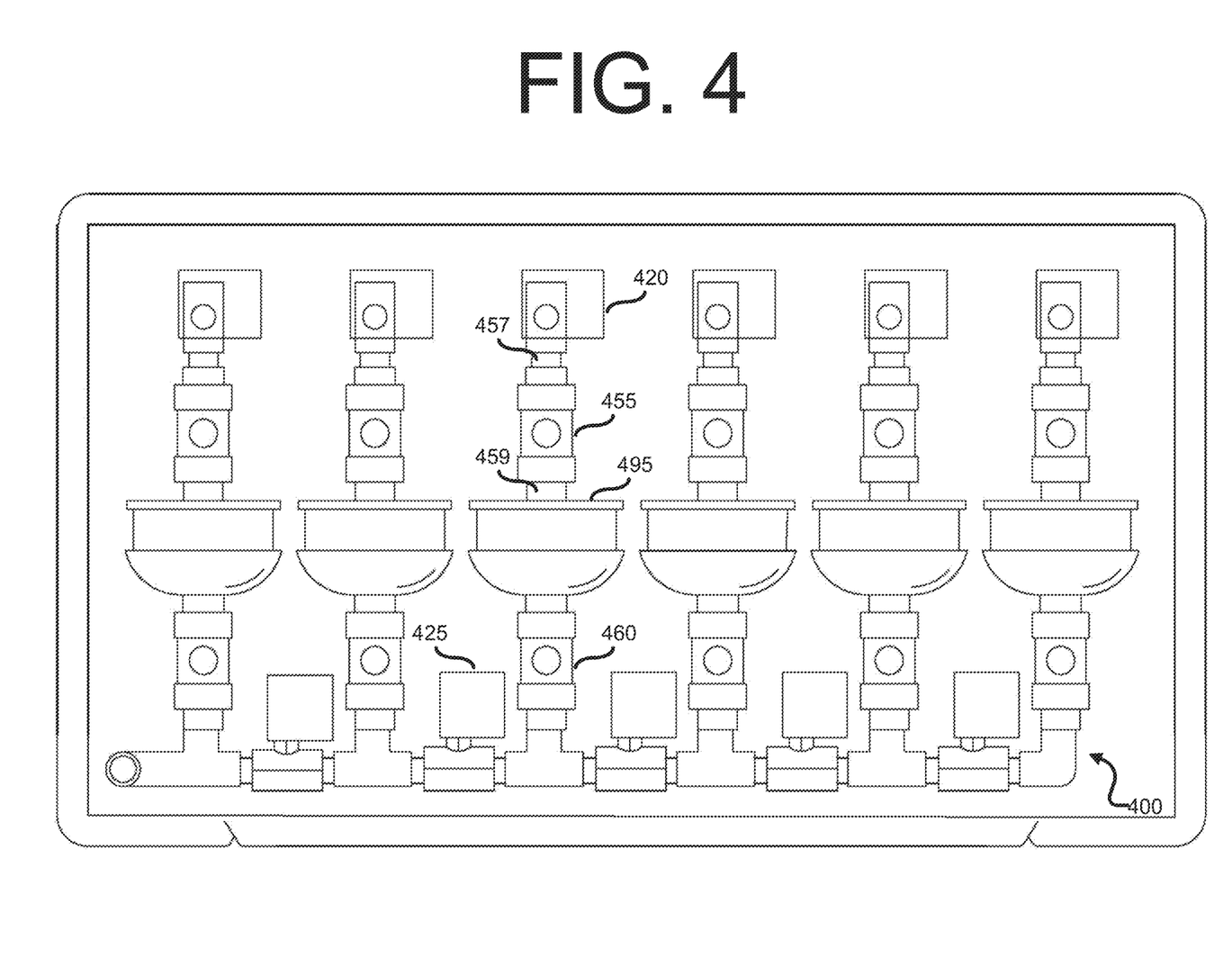
FIG. 4 illustrates an example of an array of sample collection vessel stacks of a field apparatus according to certain embodiments of this disclosure.

FIG. 4 illustrates an example of an array 400 of sample collection vessel stacks of a field apparatus according to certain embodiments of this disclosure. As shown in the non-limiting example of FIG. 4, array 400 utilizes a highly modular construction, allowing certain field apparatus according to this disclosure to be readily repairable (for example, non-functioning components can be easily swapped out) and extensible (for example, the number of sample collection vessels under the control of a single acquisition controller can readily be increased).

Referring to the non-limiting example of FIG. 4, array 400 comprises a plurality of sample collection vessel stacks (for example, the stack comprising sample collection vessel 405) inside a protective enclosure 401 of a field apparatus (for example, field apparatus 100 of FIG. 1). As shown in FIG. 4, one stack of array 400 comprises sample collection vessel 405, which is connected to a manual inlet valve 455, which is in turn connected to electronic inlet valve 420. Sample collection vessel 405 is likewise connected to manual outlet valve 460 and electronically controlled outlet valve 425. According to certain embodiments, each of the inlet and outlet portions of the components within a sample collection vessel stack have a diameter and interior profile (for example, ½ inch smooth openings) to allow the parts to be connected by a single common connector. For example, in the non-limiting example of FIG. 4, the inlet and outlet portions all of the components of each sample collection vessel stack are have a smooth profile and an interior diameter of 13/16 inches, thereby allowing components to be connected by sections of standard ½ inch PVC pipe. As shown in FIG. 4, manual inlet valve 455 is connected to electronic inlet valve 420 via a first section of ½ inch PVC pipe 457 and to sample collection vessel 405 via a second section of ½ inch PVC pipe 459.

Figure 5:
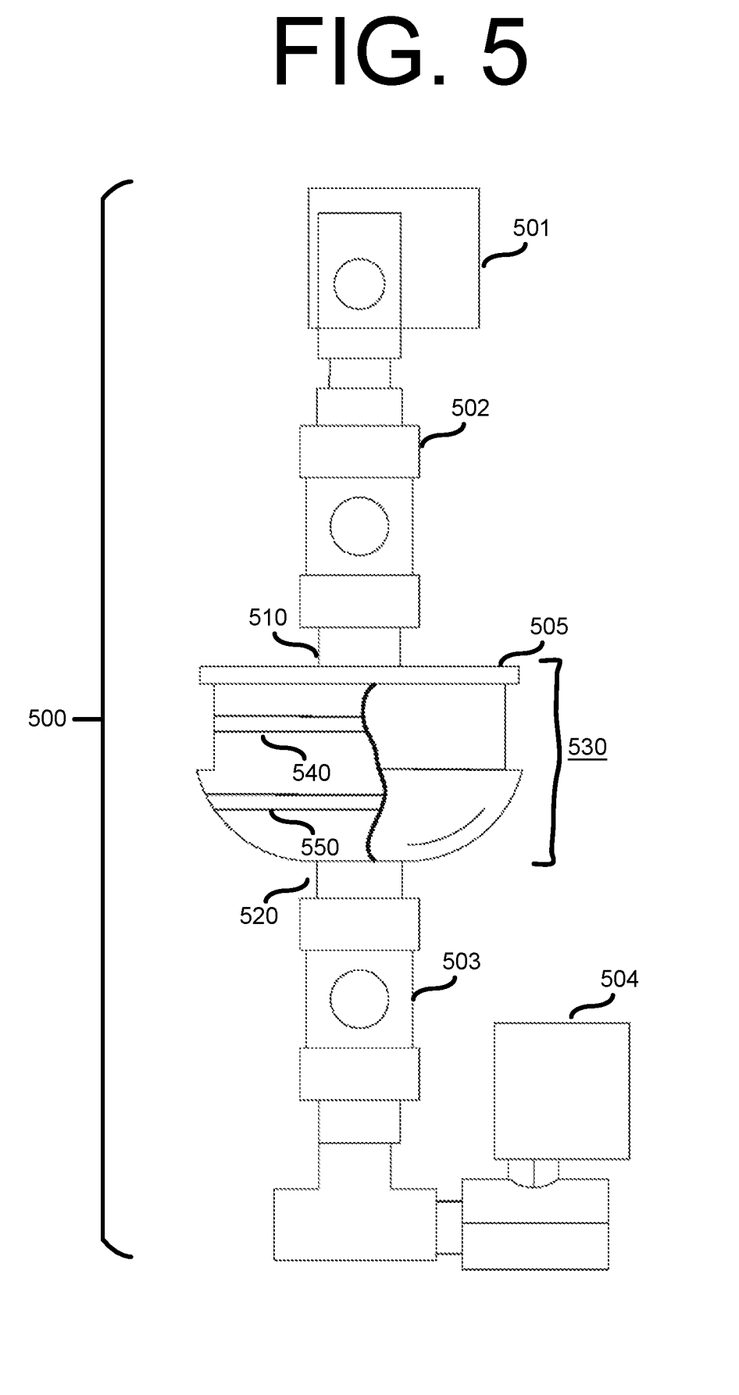
FIG. 5 illustrates an example of a sample collection vessel according to some embodiments of this disclosure.

FIG. 5 illustrates an example of a sample collection vessel 505 according to some embodiments of this disclosure.

Referring to the non-limiting example of FIG. 5, sample collection vessel 505 is illustrated as comprising a component within a sample collection vessel stack 500. In certain embodiments, sample collection vessel 505 includes an inlet portion 510 which connects, sample collection vessel 505 to electronically controlled inlet valve 501 indirectly, via manual inlet valve 502. According to certain embodiments, inlet portion 510 is hollow, and has an interior portion which guides liquids (for example, aqueous media or biopreservative) into plenum 530.

In the illustrative example of FIG. 5, plenum 530 is shown in partial cross-section, with the exterior portion shown on the right, and an interior cutaway on the left. According to some embodiments, plenum 530 has an inverted bell shape, with a flat upper and curved lower. In certain embodiments, plenum 530 includes a filter 540 which is connected to an interior circumference of plenum 530 such that any fluid entering plenum 530 from inlet portion 510 and exiting via outlet portion 520 must pass through filter 540. In some embodiments, filter 540 is a paper filter. In various embodiments, filter 540 is a nylon mesh filter.

In some embodiments, plenum 530 comprises a second filter 550 disposed along a second interior circumference of plenum 530 and on the path of liquid passing through plenum 530. According to various embodiments, second filter 550 has finer mesh size than filter 540 (for example, in certain embodiments, filter 540 has an 80 micron mesh size and filter 550 has a 30 micron mesh size).

In various embodiments according to this disclosure, sample collection vessel 505 comprises an outlet portion 520, which is hollow, and whose interior portion guides liquid to electronically controlled outlet valve 504. According to some embodiments, outlet portion 520 is connected directly to electronically controlled outlet valve 504. In various embodiments, outlet portion is connected indirectly (for example, via manual outlet valve 503), to electronically controlled outlet valve 504.

Figure 6:
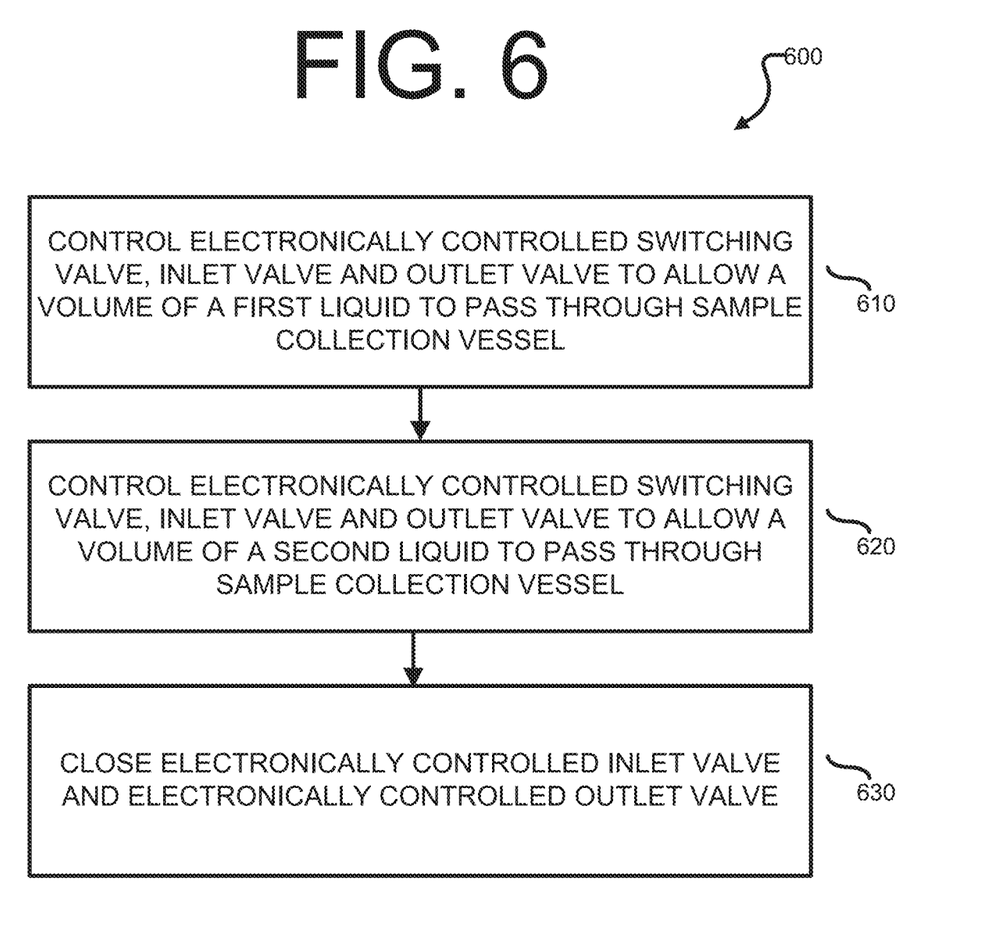
FIG. 6 illustrates operations of a method for remotely capturing an unstable analyte in a sample of an aqueous medium according to various embodiments of this disclosure.

FIG. 6 illustrates operations of a method 600 for remotely capturing an unstable analyte in a sample of an aqueous medium according to various embodiments of this disclosure. According to certain embodiments, the operations of method 600 are performed by a field apparatus (for example, field apparatus 100 in FIG. 1) operating according to program logic executed by a processor (for example, acquisition controller 110 in FIG. 1). In some embodiments, the operations of method 600 comprise one sample collection operation of a battery of sample collection operations to be performed by a field apparatus (for example, field apparatus 200 in FIG. 2), which has been configured and left to run automatically in the field for the duration of the test cycle (e.g., a technician configures the field apparatus, leaves, and then returns after all of the samples have been collected).

Referring to the non-limiting example of FIG. 6, method 600 comprises operation 610, wherein an acquisition controller controls an electronically controlled switching valve (for example, switching valve 130a in FIG. 1), an electronically controlled inlet valve (for example, electronically controlled inlet valve 501 in FIG. 5), and an electronically controlled outlet valve (for example, electronically controlled outlet valve 425 in FIG. 4) to control the passage of a volume of a first liquid to the electronically controlled inlet valve. According to certain embodiments, operation 610 is performed as part of a "Fill" step of a pre-programmed sequence of operations, and the first liquid is an aqueous medium (for example, lake or ocean water). In some embodiments, operation 610 concludes when a timer is reached (for example, when the aqueous medium has been allowed to pass through a sample collection vessel for 5 minutes). In various embodiments, the duration of operation 610 is keyed off of a measurement of the volume (for example, a measurement based off of sensor data from inlet flow meter 117 in FIG. 1) of the first liquid passing through the sample control vessel.

According to various embodiments, the performance of operation 810 depends on the value of an operational parameter. Examples of operational parameters which can control or restrict the performance of operation 610 include, without limitation, measured air temperature (for example, if the temperature is below freezing, operation 610 may be suspended to avoid component damage), passage of a specified time (for example, a predetermined interval between sample collection operations, to ensure that data is obtained across a range of times), satisfaction of a previous operation by the field apparatus (for example, execution of a flush cycle, to ensure that the system is "clean"), or the status of another component of the field apparatus (for example, an indication of whether a battery or power supply has sufficient charge).

As shown in the non-limiting example of FIG. 6, method 600 includes operation 620, wherein the acquisition controller controls an electronically controlled switching valve (for example, switching valve 130a in FIG. 1), an electronically controlled inlet valve (for example, electronically controlled inlet valve 120a in FIG. 1), and an electronically controlled outlet valve (for example, electronically controlled outlet valve 125a in FIG. 1) to allow a volume of a second liquid to pass through the sample collection vessel. According to various embodiments, the second liquid is a volume of a biopreservative (for example, biopreservative stored in biopreservative reservoir 135 in FIG. 1).

In some embodiments, method 600 also includes operation 630, wherein the acquisition controller causes an electronically controlled switching valve, an electronically controlled inlet valve and an electronically opened outlet valve to close. According to various embodiments, operation 630 is performed at the end of a sample collection cycle for a given sample collection vessel, and has the effect of "sealing up" the collection vessel to protect the preserved matter inside, and to ready the field apparatus for a subsequent sample to be collected in another sample collection vessel.

According to various embodiments, the operations of method 600 can be variously repeated, omitted, or concatenated with other switching and pumping operations of the field apparatus. TABLE 1 below, illustrates a set of steps orchestrated by an acquisition controller to collect a sample in one of a plurality of sample collection vessels of a field apparatus. According to various embodiments, the "Lake Pump" of Table 1 is a sample pump (for example, sample pump 103 in FIG. 1), the "Pres. Pump" is a biopreservative pump (for example, biopreservative pump 137 in FIG. 1), the "Main Inlet Valve" is an electronically controlled inlet valve (for example, inlet valve 115 in FIG. 1), the "Flush Valve" is an electronically controlled flush valve (for example, flush valve 175 in FIG. 1), the "Drain Valve" is an electronically controlled valve at the outlet of a drain line (for example, drain line 165 in FIG. 1), the "Air Valve" is an electronically controlled valve configured to relieve pressure in an inlet line of the field apparatus (for example, air valve 140 in FIG. 1), "#1 Inlet Valve" is an electronically controlled inlet valve (for example, electronically controlled inlet valve 120a in FIG. 1) for sample collection vessel "#1" and "#1 Outlet Valve" is an electronically controlled outlet valve (for example, electronically controlled outlet valve 125a in FIG. 1) for sample collection vessel "#1".

TABLE 1

| Step | State | Lake Pump | Pres. Pump | Main Inlet Valve | Flush Valve | Drain Valve | Air Valve | #1 Inlet Valve | #1 Outlet Valve |
| --- | --- | --- | --- | --- | --- | --- | --- | --- | --- |
| 1 | Wait | Off | Off | Closed | Closed | Closed | Closed | Closed | Closed |
| 2 | Flush | On | Off | Open | Open | Closed | Closed | Closed | Closed |
| 3 | Fill #1 | On | Off | Open | Closed | Open | Closed | Open | Open |
| 4 | Drain #1 | Off | Off | Closed | Closed | Open | Open | Open | Open |
| 5 | Pres. Pt. 1 | Off | On | Closed | Closed | Closed | Closed | Open | Closed |
| 6 | Pres. Pt. 2 | Off | On | Closed | Closed | Open | Closed | Open | Open |
| 7 | Wait | Off | Off | Closed | Closed | Closed | Closed | Closed | Closed |
| 8 | Flush | On | Off | Open | Open | Closed | Closed | Closed | Closed |
| ... | ... | ... | ... | ... | ... | ... | ... | ... | ... |

None of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle.

What is claimed is:

1. An apparatus for remotely capturing an unstable analyte in a sample of an aqueous medium, comprising:
a sample collection vessel comprising:
an inlet portion,
an outlet portion, and
a plenum comprising a first filter, the first filter disposed between the inlet portion and outlet portion;
an electronically controlled inlet valve connected to the inlet portion and configured to control passage of liquid into the sample collection vessel via the inlet portion;
an electronically controlled outlet valve connected to the outlet portion configured to control passage of liquid out of the sample collection vessel via the outlet portion;
an electronically controlled sample inlet valve connected to the electronically controlled inlet valve and configured to control passage of a first liquid to the electronically controlled inlet valve;
an electronically controlled switching valve configured to control passage of a second liquid to the electronically controlled inlet valve; and
an acquisition controller configured to:
control the electronically controlled sample inlet valve, electronically controlled switching valve, electronically controlled inlet valve, and electronically controlled outlet valve to allow a volume of the first liquid to pass through the sample collection vessel,
control the electronically controlled sample inlet valve, electronically controlled switching valve, electronically controlled inlet valve, and electronically controlled outlet valve to allow a volume of the second liquid to pass through the sample collection vessel, and
close the electronically controlled inlet valve and electronically controlled outlet valve.

2. The apparatus of claim 1, further comprising:
one or more additional sample collection vessels; each additional sample collection vessel comprising:
an inlet portion;
an outlet portion; and
a plenum comprising a filter, the filter disposed between the inlet portion and outlet portion; and
for each additional sample collection vessel of the additional sample collection vessels:
an electronically controlled inlet valve configured to control passage of liquid into the additional sample collection vessel via the inlet portion, and
an electronically controlled outlet valve configured to control passage of liquid out of the additional sample collection vessel via the outlet portion,
wherein the acquisition controller is further configured to:

for each sample collection vessel of the additional sample collection vessels, to control the electronically controlled sample inlet valve, electronically controlled switching valve, electronically controlled inlet valve for the additional sample collection vessel, and electronically controlled outlet valve for the additional sample collection vessel to allow a volume of the first liquid to pass through the additional sample collection vessel;

control the electronically controlled sample inlet valve, electronically controlled switching valve, electronically controlled inlet valve for the additional sample collection vessel, and electronically controlled outlet valve for the additional sample collection vessel to allow a volume of the second liquid to pass through the additional sample collection vessel; and close the electronically controlled inlet valve for the additional sample collection vessel and electronically controlled outlet valve for the additional sample collection vessel.

3. The apparatus of claim 1, wherein the first liquid is an aqueous sample, and the second liquid is a biopreservative solution.

4. The apparatus of claim 1, wherein the plenum further comprises a second filter, the second filter having at least one of a different mesh number or mesh size than the first filter.

5. The apparatus of claim 1, further comprising a solar power source, wherein the solar power source is connected to and provides power to one or more of the electronically controlled sample inlet valve, electronically controlled inlet valve, the electronically controlled outlet valve, the acquisition controller or the electronically controlled switching valve.

6. The apparatus of claim 1, wherein the acquisition controller is further configured to:
control the electronically controlled inlet valve and electronically controlled outlet valve to allow a volume of the first liquid to pass through the sample collection vessel according to a first parameter,
wherein the first parameter comprises at least one of a temperature of the first liquid, a measured volume of the first liquid, a sample time, a flush time, or an available charge of a battery.

7. The apparatus of claim 1, wherein at least one of the electronically controlled sample inlet valve, electronically controlled inlet valve, electronically controlled outlet valve or electronically controlled switching valve comprise a ball valve.

8. A method of remotely capturing an unstable analyte in a sample of an aqueous medium, the method comprising:
controlling an electronically controlled switching valve, an electronically controlled sample inlet valve, an electronically controlled inlet valve, and an electronically controlled outlet valve of an apparatus to allow a volume of a first liquid to pass through a sample collection vessel, the sample collection vessel comprising an inlet portion connected to the electronically controlled inlet valve, an outlet portion connected to the electronically controlled outlet valve, and a plenum comprising a first filter, the first filter disposed between the inlet portion and outlet portion;
controlling the electronically controlled switching valve, the electronically controlled sample inlet valve, electronically controlled inlet valve, and electronically controlled outlet valve to allow a volume of a second liquid to pass through the sample collection vessel; and
closing the electronically controlled inlet valve and electronically controlled outlet valve,
wherein the electronically controlled inlet valve is configured to control passage of liquid into the sample collection vessel via the inlet portion,
wherein the electronically controlled outlet valve is configured to control passage of liquid out of the sample collection vessel via the outlet portion,
wherein the electronically controlled sample inlet valve is configured to control passage of a first liquid to the electronically controlled inlet valve, and
wherein the electronically controlled switching valve is configured to control passage of a second liquid to the electronically controlled inlet valve.

9. The method of claim 8, wherein the apparatus comprises one or more additional sample collection vessels, each additional collection vessel comprising an inlet portion, an outlet portion, and a plenum comprising a filter, the filter disposed between the inlet portion and outlet portion, and connected to an electronically controlled inlet valve and an electronically controlled outlet valve, the method further comprising, for each sample vessel of the additional sample collection vessels:
controlling the electronically controlled sample inlet valve, the electronically controlled switching valve, the electronically controlled inlet valve connected to the additional sample collection vessel, and the electronically controlled outlet valve connected to the additional sample collection vessel to allow a volume of a first liquid to pass through the additional sample collection vessel;
controlling the electronically controlled sample inlet valve, the electronically controlled switching valve, the electronically controlled inlet valve connected to the additional sample collection vessel, and electronically controlled outlet valve connected to the additional sample collection vessel to allow a volume of a second liquid to pass through the additional sample collection vessel; and
closing the electronically controlled inlet valve connected to the additional sample collection vessel and electronically controlled outlet valve connected to the additional sample collection vessel.

10. The method of claim 8, wherein the first liquid is an aqueous sample and the second liquid is a biopreservative solution.

11. The method of claim 8, wherein the plenum of the sample collection vessel comprises a second filter, the second filter having at least one of a different mesh number or mesh size than the first filter.

12. The method of claim 8, further comprising controlling at least one of the electronically controlled switching valve, the electronically controlled sample inlet valve, the electronically controlled inlet valve or the electronically controlled outlet valve based on an availability of power from a solar power source connected to the apparatus.

13. The method of claim 8, further comprising:
controlling one or more of the electronically controlled sample inlet valve, the electronically controlled switching valve, the electronically controlled inlet valve, and the electronically controlled outlet valve to allow a volume of the first liquid to pass through the sample collection vessel according to a first parameter,
wherein the first parameter comprises one or more of a temperature of the first liquid, a measured volume of the first liquid, a sample time, a flush time, or an available charge of a battery.

14. A non-transitory computer-readable medium comprising program code, which when executed by a processor, causes an apparatus to:
control an electronically controlled switching valve, an electronically controlled sample inlet valve, an electronically controlled inlet valve, and an electronically controlled outlet valve of an apparatus to allow a volume of a first liquid to pass through a sample collection vessel, the sample collection vessel comprising an inlet portion connected to the electronically controlled inlet valve, an outlet portion connected to the electronically controlled outlet valve and a plenum comprising a first filter, the first filter disposed between the inlet portion and outlet portion;
control the electronically controlled sample inlet valve, the electronically controlled switching valve, electronically controlled inlet valve, and electronically controlled outlet valve to allow a volume of a second liquid to pass through the sample collection vessel; and
close the electronically controlled inlet valve and the electronically controlled outlet valve,
wherein the electronically controlled inlet valve is configured to control passage of liquid into the sample collection vessel via the inlet portion,
wherein the electronically controlled outlet valve is configured to control passage of liquid out of the sample collection vessel via the outlet portion,
wherein the electronically controlled sample inlet valve is configured to control passage of a first liquid to the electronically controlled inlet valve, and
wherein the electronically controlled switching valve is configured to control passage of a second liquid to the electronically controlled inlet valve.

15. The non-transitory computer-readable medium of claim 14, wherein the apparatus comprises one or more additional sample collection vessels, each additional collection vessel comprising an inlet portion, an outlet portion, and a plenum comprising a first filter, the first filter disposed between the inlet portion and outlet portion, and connected to an electronically controlled inlet valve and an electronically controlled outlet valve, and the non-transitory computer-readable medium comprises program code, which when executed by the processor, causes the apparatus to, for each sample vessel of the additional sample collection vessels:
control the electronically controlled sample inlet valve, the electronically controlled switching valve, the electronically controlled inlet valve connected to the additional sample collection vessel, and the electronically controlled outlet valve connected to the additional sample collection vessel to allow a volume of a first liquid to pass through the additional sample collection vessel;
control the electronically controlled sample inlet valve, the electronically controlled switching valve, the electronically controlled inlet valve connected to the additional sample collection vessel, and electronically controlled outlet valve connected to the additional sample collection vessel to allow a volume of a second liquid to pass through the additional sample collection vessel; and
close the electronically controlled inlet valve connected to the additional sample collection vessel and electronically controlled outlet valve connected to the additional sample collection vessel.

16. The non-transitory computer-readable medium of claim 14, wherein the first liquid is an aqueous sample and the second liquid is a biopreservative solution.

17. The non-transitory computer-readable medium of claim 14, wherein the plenum of the sample collection vessel comprises a second filter, the second filter having at least one of a different mesh number or mesh size than the first filter.

18. The non-transitory computer-readable medium of claim 14, further comprising program code, which when executed by the processor, causes the apparatus to control one or more of the electronically controlled sample inlet valve, the electronically controlled switching valve, electronically controlled inlet valve or the electronically controlled outlet valve based on an availability of power from a solar power source connected to the apparatus.

19. The non-transitory computer-readable medium of claim 14, further comprising program code, which when executed by the processor, causes the apparatus to control one or more of the electronically controlled sample inlet valve, the electronically controlled switching valve, the electronically controlled inlet valve, and the electronically controlled outlet valve to allow a volume of the first liquid to pass through the sample collection vessel according to a first parameter,
wherein the first parameter comprises at least one of a temperature of the first liquid, a measured volume of the first liquid, a sample time, a flush time, or an available charge of a battery.

20. The non-transitory computer-readable medium of claim 14, wherein one or more of the electronically controlled sample inlet valve, the electronically controlled inlet valve, electronically controlled outlet valve or electronically controlled switching valve comprise a ball valve.

* * * * *